US009111257B2

(12) United States Patent
Oh et al.

(10) Patent No.: US 9,111,257 B2
(45) Date of Patent: Aug. 18, 2015

(54) MEDICAL IMAGING APPARATUS AND CONTROL METHOD THEREOF

(71) Applicant: Samsung Electronics Co., Ltd., Gyeonggi-do (KR)

(72) Inventors: Keum Yong Oh, Gyeonggi-do (KR); Hei Soog Kim, Gyeonggi-do (KR); Kyoung Kyu Lee, Gyeonggi-do (KR); Min Ha Lee, Incheon (KR); Jeong A Kang, Gyeonggi-do (KR)

(73) Assignee: Samsung Electronics Co., Ltd., Yeongtong-gu, Suwon-si, Gyeonngi-do (KR)

( * ) Notice: Subject to any disclaimer, the term of this patent is extended or adjusted under 35 U.S.C. 154(b) by 0 days.

(21) Appl. No.: 13/777,059

(22) Filed: Feb. 26, 2013

(65) Prior Publication Data
US 2014/0088984 A1    Mar. 27, 2014

(30) Foreign Application Priority Data

Sep. 26, 2012  (KR) .................. 10-2012-0107036

(51) Int. Cl.
| | |
|---|---|
| *G06Q 50/00* | (2012.01) |
| *G06Q 10/10* | (2012.01) |
| *G06Q 50/22* | (2012.01) |
| *A61B 5/055* | (2006.01) |
| *G01R 33/54* | (2006.01) |

(52) U.S. Cl.
CPC ............. *G06Q 10/10* (2013.01); *A61B 5/055* (2013.01); *G01R 33/543* (2013.01); *G06Q 50/22* (2013.01); *G01R 33/546* (2013.01)

(58) Field of Classification Search
None
See application file for complete search history.

(56) References Cited

U.S. PATENT DOCUMENTS

| | | | |
|---|---|---|---|
| 2001/0018659 A1* | 8/2001 | Koritzinsky et al. | 705/3 |
| 2004/0147840 A1 | 7/2004 | Duggirala et al. | |
| 2004/0193036 A1 | 9/2004 | Zhou et al. | |
| 2005/0121505 A1* | 6/2005 | Metz et al. | 235/375 |
| 2007/0229070 A1* | 10/2007 | Miyazaki | 324/307 |
| 2008/0119717 A1* | 5/2008 | Profio et al. | 600/407 |
| 2008/0172249 A1 | 7/2008 | Glaser-Seidnitzer et al. | |
| 2010/0049050 A1 | 2/2010 | Pelissier et al. | |

FOREIGN PATENT DOCUMENTS

| | | |
|---|---|---|
| JP | 2007-143719 A | 6/2007 |
| WO | 2012/117314 A1 | 9/2012 |

OTHER PUBLICATIONS

Tuite et al., Shoulder MRI—UW Madison, Mar. 11, 2011, 3 pages.*

(Continued)

*Primary Examiner* — Mark Holcomb
*Assistant Examiner* — Jason Tiedeman
(74) *Attorney, Agent, or Firm* — Cha & Reiter, LLC.

(57) ABSTRACT

A medical imaging apparatus operates to automatically recommend protocols suitable for image capture of a subject based on information related to the subject, and a control method operates the medical imaging apparatus. The medical imaging apparatus includes a controller which determines one or more protocols to scan a subject, classifies the protocols based on plural predefined criteria, and aligns and recommends the protocols classified according to a selected criterion if any one of the plural criteria is selected, and a display unit which displays an array of the protocols recommended by the controller.

12 Claims, 10 Drawing Sheets

(56) References Cited

OTHER PUBLICATIONS

J. Biederer, et al.; "MRI of the Lung (2/3). Why . . . When . . . How?;" Insights Into Imaging, vol. 3, No. 4; Feb. 13, 2012; XP055071180.
J. Biederer, et al.; "MRI of the Lung—Ready . . . Get Set . . . Go!" Magnetom Flash; Jan. 1, 2011; XP055071186.
T. Alsinet et al., Automated Monitoring of Medical Protocols: A Secure and Distributed Architecture, Oct. 18, 2002, 367-392, Lleida, Spain.
Rehwald G. Wolfgang et al., Cardiovascular MRI: Its Current and Future Use in Clinical Practice, 2007, 307-321.

* cited by examiner

MEDICAL IMAGING APPARATUS AND CONTROL METHOD THEREOF

CLAIM OF PRIORITY

This application claims, pursuant to 35 U.S.C. 119(a), priority to and the benefit of the earlier filing date of Korean Patent Application No. 10-2012-0107036, filed on Sep. 26, 2012 in the Korean Intellectual Property Office, the disclosure of which is incorporated herein by reference.

BACKGROUND OF THE INVENTION

1. Field of the Invention

The present invention relates to a magnetic imaging apparatus, and in particular to a magnetic resonance imaging apparatus used to diagnose various diseases using magnetic resonance images and a control method thereof.

2. Description of the Related Art

In general, medical imaging apparatuses are apparatuses that acquire information on a patient and provide an image. Medical imaging apparatuses include X-ray apparatuses, ultrasonic diagnostic apparatuses, computed tomography apparatuses, magnetic resonance imaging apparatuses, and the like.

Among these apparatuses in the prior art, magnetic resonance imaging apparatuses play an important role in medical fields using medical imaging because magnetic resonance imaging apparatuses have relatively free image capture conditions and provide excellent contrast in soft tissues and various diagnostic information images.

Magnetic Resonance Imaging (MRI) generates images representing the density of atoms and molecules based on characteristics of their atomic nuclei and other physical and chemical properties by causing nuclear magnetic resonance of, for example, hydrogen atomic nuclei in a test subject, such as the body of a patient, using Radio Frequencies (RF) as specific ionization radiation and magnetic fields that are not harmful to human bodies.

More specifically, MRI apparatuses are diagnostic imaging apparatuses that diagnose the interior of a human body by applying a predetermined frequency and energy to atomic nuclei under the influence of a predetermined range of a magnetic field and converting energy emitted from the atomic nuclei into signals.

A proton is a constituent of an atomic nucleus and has a spin angular momentum and magnetic dipoles. Therefore, atomic nuclei are aligned in the direction of a magnetic field applied thereto and perform precessional motion in the direction of the magnetic field. With the precessional motion, an image of a human body may be acquired via nuclear magnetic resonance.

Meanwhile, MRI apparatuses may need a longer image capture time than other diagnostic imaging apparatuses. Furthermore, a certain time may be required to prepare for image capture, which may cause patients who undergoing diagnosis to fear image capture. For example, it may be necessary for a patient who is positioned within an RF coil to prepare for image capture alone within a bore while an operator inputs information on the patient and manually selects an image capture protocol. The patient may experience anxiety during the preparation time, and the entire time consumed for image capture may be lengthened. This work flow in the prior art may cause a reduction in the turnover ratio of patients.

When selection of an image capture protocol is carried out by the judgment of the operator, image capture suitability of the protocol may depend on the ability and skill of the operator. That is, as the operator selects the protocol based on his/her experience and knowledge, different images may be acquired according to the kind of sequence in the case of MRI diagnosis, and therefore the ability and skill of the operator may be an important factor to acquire an image suitable for diagnosis. This reliance on operator ability is not limited to the MRI apparatuses and may be applied to all other medical imaging apparatuses.

SUMMARY OF THE INVENTION

It is an aspect of the present invention to provide a medical imaging apparatus to automatically recommend protocols suitable for image capture of a subject based on information related to the subject, and a control method thereof.

Additional aspects of the invention will be set forth in part in the description which follows and, in part, will be obvious from the description, or may be learned by practice of the invention. In accordance with one aspect of the invention, a medical imaging apparatus includes a controller which determines one or more protocols to scan a subject, classifies the protocols based on plural predefined criteria, and aligns and recommends the protocols classified according to a selected criterion if any one of the plural criteria is selected, and a display unit which displays an array of the protocols recommended by the controller.

The plural criteria to classify the protocols may include image capture time, resolution, image capture noise, power consumption, image quality, and the amount of data.

If any one of the plural criteria is selected, the controller may align the protocols, classified according to the selected criterion, based on similarity between the protocols.

The controller may receive and analyze information related to the subject to calculate information required to scan the subject, and may determine one or more protocols to scan the subject based on the information if the information required to scan the subject is calculated.

The information related to the subject may include the sex, age, and medical record of the subject, and subject diagnosis information given by a medical team.

The diagnosis information may include information on diseased areas, a possible illness, and protocols selected by a medical team.

The display unit may display an image related to an image capture area of the subject, information related to the subject, diagnosis information given by a medical team, and the array of the protocols recommended by the controller.

The display unit may provide a user interface to allow a user to select a desired protocol from among the array of the recommended protocols.

In accordance with another aspect of the present invention, a control method of a medical imaging apparatus includes determining one or more protocols to scan a subject, classifying the protocols based on plural predefined criteria if the protocols are determined, and aligning and recommending the protocols classified according to a selected criterion if any one of the plural criteria is selected.

The plural criteria to classify the protocols may include image capture time, resolution, image capture noise, power consumption, image quality, and the amount of data.

Aligning and recommending the protocols classified according to the selected criterion if any one of the plural criteria is selected may include aligning the protocols, classified according to the selected criterion if any one of the plural criteria is selected, based on similarity between the protocols.

Determining one or more protocols to scan the subject may include receiving and analyzing information related to the subject to calculate information required to scan the subject, and determining one or more protocols to scan the subject based on the information if the information required to scan the subject is calculated.

The information related to the subject may include the sex, age, and medical record of the subject, and subject diagnosis information given by a medical team.

The diagnosis information may include information on diseased areas, a possible illness, and protocols selected by a medical team.

The control method may further include displaying an array of the recommended protocols, an image related to an image capture area of the subject, information related to the subject, and diagnosis information given by a medical team on a display unit.

Displaying the array of the recommended protocols on the display unit may include displaying, on the display unit, the protocols aligned and recommended via a user interface to allow a user to select a desired protocol from among the array of the recommended protocols.

BRIEF DESCRIPTION OF THE DRAWINGS

These and/or other aspects of the invention will become apparent and more readily appreciated from the following description of the exemplary embodiments, taken in conjunction with the accompanying drawings of which.

DETAILED DESCRIPTION OF THE INVENTION

Figure 1:
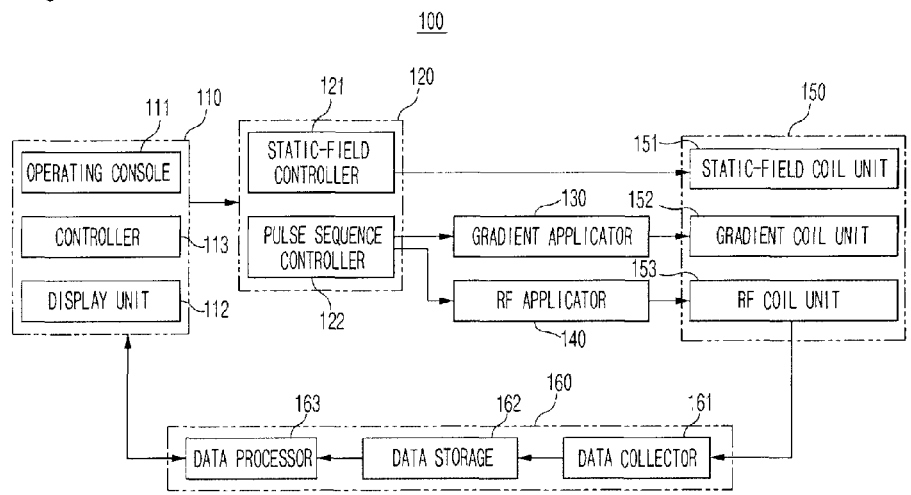
FIG. 1 is a block diagram of a magnetic resonance imaging apparatus according to an exemplary embodiment of the present invention.

Reference will now be made in detail to the exemplary embodiments of the present invention in which a magnetic resonance imaging apparatus is given as one example of a medical imaging apparatus, examples of which are illustrated in the accompanying drawings, wherein like reference numerals refer to like elements throughout. However, it will be appreciated that technical ideas of the exemplary embodiments of the present invention are not limited to the magnetic resonance imaging apparatus, and may be applied to various other medical imaging apparatuses, such as computed tomography apparatuses, X-ray image capture apparatuses, and the like.

In the following description, a detailed explanation of known related functions and constructions may be omitted to avoid unnecessarily obscuring the subject matter of the present invention. The present invention may, however, be embodied in many different forms and should not be construed as limited to the exemplary embodiments set forth herein. In addition, terms described herein, which are defined with reference to the functions of the present invention, may be implemented differently depending on a user or operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

FIG. 1 is a block diagram of a magnetic resonance imaging apparatus according to an exemplary embodiment of the present invention.

Referring to FIG. 1, the magnetic resonance imaging apparatus 100 according to the exemplary embodiment of the present invention includes a magnet assembly 150 to generate a magnetic field and cause resonance of atomic nuclei, a coil controller 120 to control operations of coils constituting the magnet assembly 150, an image processor 160 to form a magnetic resonance image upon receiving echo-signals generated from the atomic nuclei, and a workstation 110 to control general operations of the magnetic resonance imaging apparatus 100.

The magnet assembly 150 includes a static field coil unit 151 to generate a static field within the magnet assembly 150, a gradient coil unit 152 to generate a gradient magnetic field in the static field, a conductor located in a space between the static field coil unit 151 and the gradient coil unit 152, and an RF coil unit 153 to excite atomic nuclei by applying an RF pulse thereto and receive echo signals from the atomic nuclei.

The coil controller 120 includes a static field controller 121 to control the strength and direction of the static field generated by the static field coil unit 151, and a pulse sequence controller 122 to configure a pulse sequence so as to control the gradient coil unit 152 and the RF coil unit 153 based on the pulse sequence.

The magnetic resonance imaging apparatus 100 according to the exemplary embodiment of the present invention may include a gradient applicator 130 to apply a gradient signal to the gradient coil unit 152, and an RF applicator 140 to apply an RF signal to the RF coil unit 153. As the gradient applicator 130 and the RF applicator 140 are controlled by the pulse sequence controller 122, the gradient magnetic field generated in the static field and the RF pulse applied to the atomic nuclei may be adjusted.

The magnetic resonance imaging apparatus 100 according to the exemplary embodiment of the present invention includes the workstation 110 to allow an operator of the magnetic resonance imaging apparatus 100 to manipulate equipment, whereby control commands, related to general operations of the magnetic resonance imaging apparatus 100, may be input to the workstation 110 by the operator. In particular, the workstation 110 may receive information related to a patient, and determine and recommend an image capture protocol suitable for the information. A detailed description thereof will follow.

Figure 2:
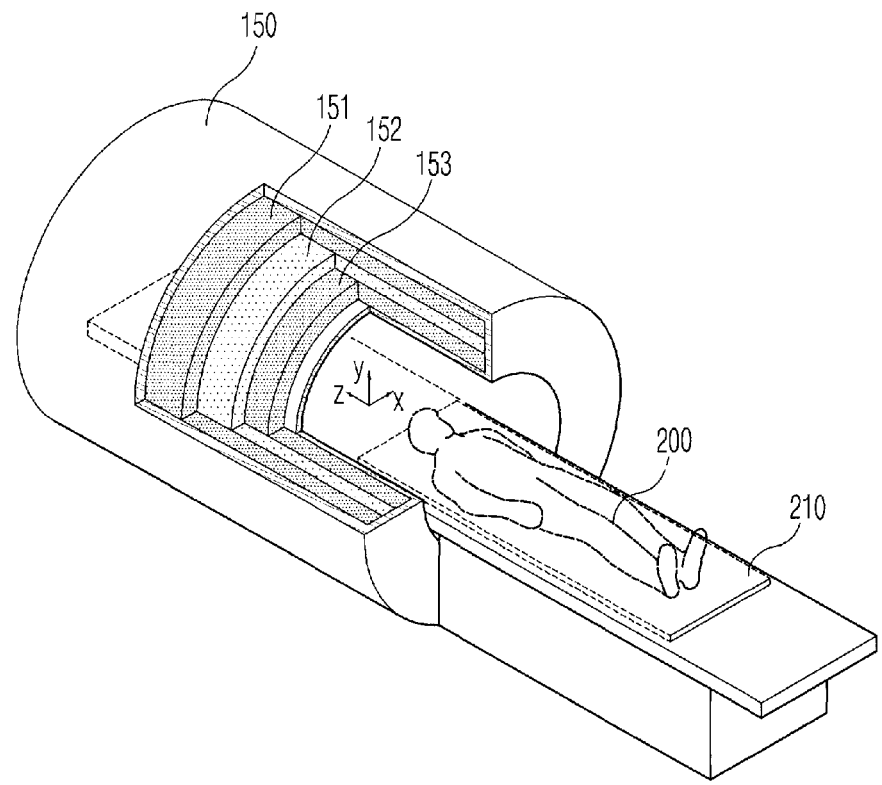
FIG. 2 is a cut-away view schematically illustrating an external appearance and portions of the internal components of a magnet assembly of the magnetic resonance imaging apparatus.

The workstation 110 may include an operating console 111 to assist the operator in manipulating and controlling the magnetic resonance imaging apparatus 100, a display unit 112 to display a control state and an image formed by the image processor 160 to assist a user in diagnosing the physical condition of a subject 200, as shown in FIG. 2, and a controller 113 to determine image capture protocols suitable for the subject 200 based on information related to the subject 200 and display the determined image capture protocols via the display unit 112 to recommend the protocols to the operator.

Figure 3:
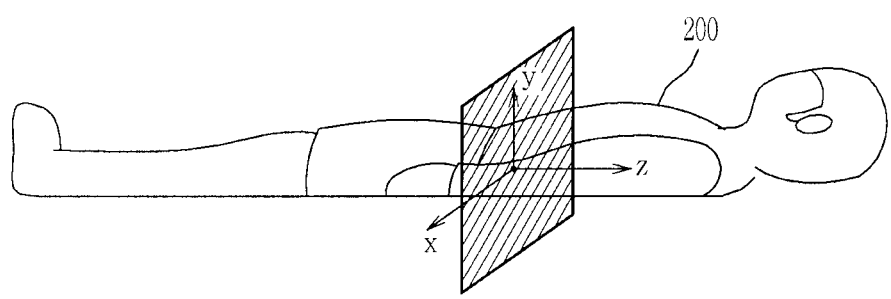
FIG. 3 is a view illustrating a space, in which a subject is placed, on the basis of X, Y and Z axes.

FIG. 2 is a cut-away view schematically illustrating an external appearance and portions of the internal components of the magnet assembly 150 of the magnetic resonance imaging apparatus 100, and FIG. 3 is a view illustrating a space, in which the subject 200 is placed, on the basis of X, Y and Z axes. FIG. 4 is a view illustrating configurations of the magnet assembly 150 and the gradient coil unit 152, and FIG. 5 is a view illustrating gradient coils constituting the gradient coil unit 152 and pulse sequences related to operations of the respective gradient coils.

A detailed operation of the magnetic resonance imaging apparatus 100 according to the exemplary embodiment of the present invention will now be described with reference to the previously described FIG. 1.

The magnet assembly 150 generally takes the form of a cylinder having an empty interior space referred to as a cavity or bore. A transfer unit 210, such as a sliding table or other movable structures, may be provided to transfer the subject 200 lying thereon into the cavity or bore to enable acquisition of a magnetic resonance signal.

As described herein in connection with FIG. 1, the magnet assembly 150 includes the static field coil unit 151, the gradient coil unit 152, and the RF coil unit 153.

The static field coil unit 151 may take the form of coils surrounding the periphery of the cavity. If current is applied to the static field coil unit 151, a static field is generated in the interior of the magnet assembly 150, i.e. in the cavity or bore.

The direction of the magnetic field is generally parallel to a longitudinal axis of the generally cylindrically-shaped magnet assembly 150.

The static field generated in the cavity causes constituent atoms of the subject 200, and more particularly, atomic nuclei of hydrogen atoms to be aligned in the direction of the static field and to perform precession of the atomic nuclei in the direction of the magnetic field. A precession speed of the atomic nuclei may be designated by a precession frequency that is also referred to as a Larmor frequency, and may be represented by the following Equation 1.

$$\omega = \gamma B_0 \qquad (1)$$

Here, $\omega$ is a Larmor frequency or angular precessional frequency of a proton or an atomic nucleus, $\gamma$ is a proportional constant also known as a gyromagnetic ratio, and $B_0$ is the strength of an external magnetic field. The proportional constant varies according to the kinds of atomic nuclei used in MRI, a unit of the strength of the external magnetic field is a Tesla (T) or a Gauss (G), and a unit of the precession frequency is a Hertz (Hz).

For example, a proton in the atomic nucleus of hydrogen has a precession frequency of 42.58 MHz within an external magnetic field having the strength of 1 T. Since hydrogen occupies the greatest ratio among constituent atoms of the human body, MRI typically attempts to acquire a magnetic resonance signal using the precession of hydrogen nuclei, which is usually a single proton.

The gradient coil unit 152 generates a gradient magnetic field by applying a gradient to the static field generated in the cavity or bore.

As illustrated in FIG. 3, an axis parallel to a vertical direction from the head to the feet of the subject 200, i.e. an axis parallel to the direction of the static field may be determined as a Z-axis, while an axis parallel to a horizontal direction of the subject 200 while lying down, that is, from one side to the other of the subject 200, may be determined as an X-axis, and an axis parallel to a vertical direction of the subject 200 while lying down, that is, from the posterior to the anterior of the subject 200, may be determined as a Y-axis.

To acquire three-dimensional spatial information, gradient magnetic fields with respect to the X, Y and Z axes may be required. Thus, the gradient coil unit 152 includes three pairs of gradient coils, with each pair corresponding to a respective axis.

Figure 4A:
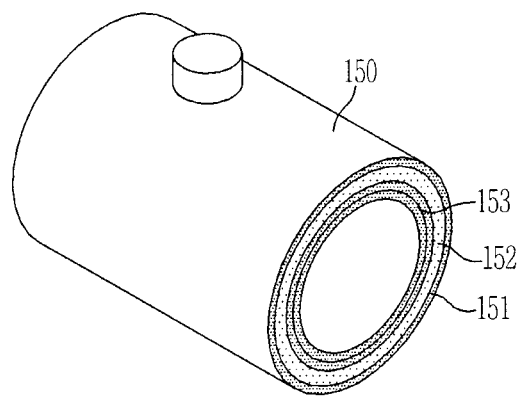
FIGS. 4A-4B are views illustrating configurations of a magnet assembly and a gradient coil unit.
Figure 5:
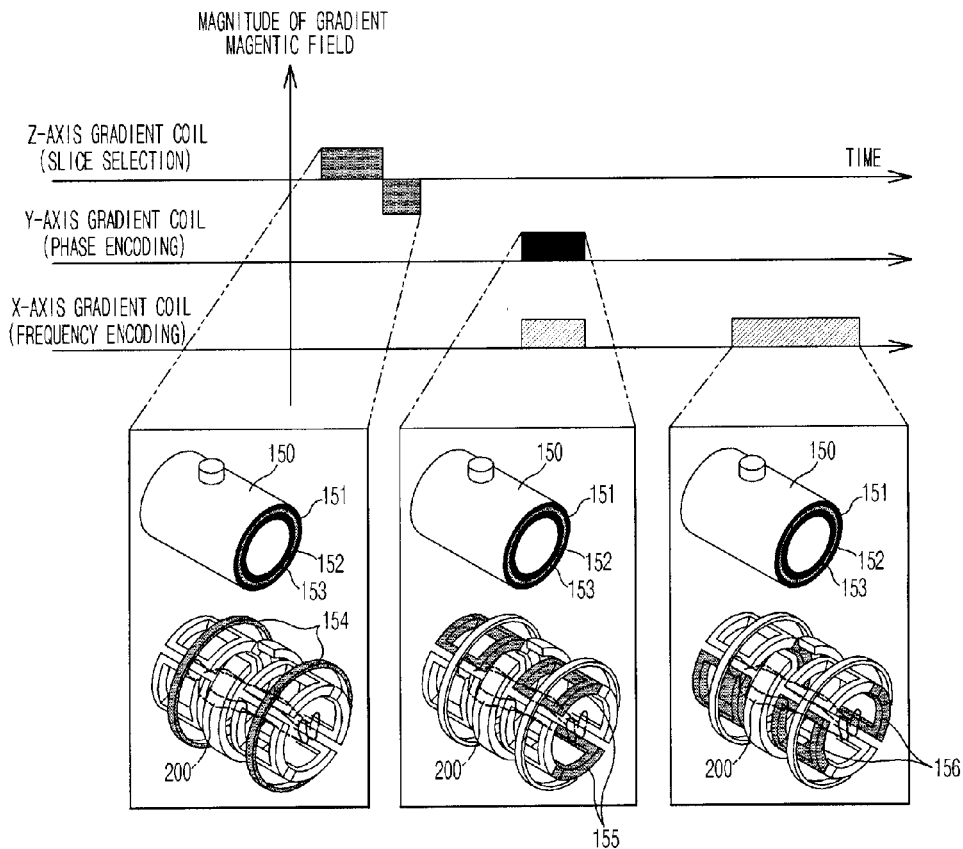
FIG. 5 is a view illustrating gradient coils constituting the gradient coil unit and pulse sequences related to operations of the respective gradient coils.

FIG. 4A illustrates an external view of the magnet assembly 150 of FIG. 2, having the static field coil unit 151 generally surrounding the gradient coil unit 152, which generally surrounds the RF coil unit 153.

Figure 4B:
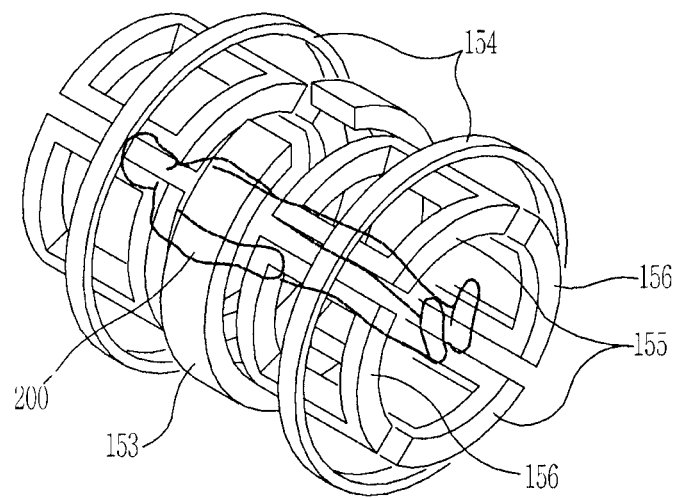

As illustrated in FIGS. 4B and 5, the gradient coil unit 152 includes Z-axis gradient coils 154, Y-axis gradient coils 155, and X-axis gradient coils. In the exemplary embodiment, the Z-axis gradient coils 154 are generally in the form of a pair of ring-shaped coils, and Y-axis gradient coils 155 are located above and below the subject 200. X-axis gradient coils 156 are located at left and right sides of the subject 200 and at least one RF coil of the RF coil unit 153 is positioned to surround at least a portion of the Y-axis gradient coils 155 and the X-axis gradient coils 156. Alternatively, the at least one RF coil of the RF coil unit 153 is positioned in a longitudinal gap in at least a portion of the Y-axis gradient coils 155 and the X-axis gradient coils 156. The patient 200 is disposed in a space within the at least one RF coil of the RF coil unit 153, the Y-axis gradient coils 155, and the X-axis gradient coils 156.

If direct current having opposite polarities is applied in opposite directions to the two Z-axis gradient coils 154, a variation of a magnetic field occurs in the Z-axis, causing generation of a gradient magnetic field, as shown in the top graph of FIG. 5 for the Z-axis gradient coil 154, with the top graph plotting the magnitude of the gradient magnetic field over time, and illustrating a magnetic field pulse waveform. FIG. 5 illustrates, using pulse sequences, generation of the Z-axis gradient magnetic field during operation of the Z-axis gradient coils 154.

As the gradient of the Z-axis magnetic field increases, selection of a thinner slice of a portion of the imaged patient 200 may be possible. Therefore, the Z-axis gradient coils 154 are used to select a slice.

If a slice is selected via the gradient magnetic field generated by the Z-axis gradient coils 154, all constituent spins of the slice have the same frequency and the same phase, and may be indistinguishable from one another.

In this case, if a gradient magnetic field is generated in the Y-axis by the Y-axis gradient coils 155, the gradient magnetic field causes a phase shift such that lines of the slice have different phases.

That is, once the Y-axis gradient magnetic field has been generated, the spins of a splice line, to which the higher strength of the gradient magnetic field is applied, undergo phase variation at a high frequency, and the spins of the splice line, to which the lower strength of the gradient magnetic field is applied, undergo phase variation at a low frequency. After the Y-axis gradient magnetic field disappears, the respective lines of the selected slice have different phases due to the occurrence of a phase shift, which enables distinction between the respective lines. As such, the gradient magnetic field generated by the Y-axis gradient coils 155 is used for phase encoding. FIG. 5 illustrates, using pulse sequences, generation of the Y-axis gradient magnetic field during operation of the Y-axis gradient coils 155.

Selection of the slice is carried out by the gradient magnetic field generated by the Z-axis gradient coils 154, and phase distinction of the constituent lines of the selected slice is carried out by the gradient magnetic field generated by the Y-axis gradient coils 155. However, the respective constituent spins of each line have the same frequency and the same phase, and may be indistinguishable from one another.

In this case, if a gradient magnetic field is generated in the X-axis by the X-axis gradient coils 156, the gradient magnetic field causes the respective constituent spins of each line to have different frequencies, which enables distinction between the respective spins. As such, the gradient magnetic field generated by the X-axis gradient coils 156 is used for frequency encoding.

As described above, the gradient magnetic fields generated by the Z, Y and X axes gradient coils realize spatial encoding to encode spatial positions of the respective spins via slice selection, phase encoding, and frequency encoding, respectively.

The gradient coil unit 152 is connected to the gradient applicator 130, and the gradient applicator 130 applies a drive signal to the gradient coil unit 152 in response to a control signal transmitted from the pulse sequence controller 122, to enable generation of the gradient magnetic field. The gradient applicator 130 may include three driving circuits corresponding to the three pairs of gradient coils 154, 155 and 156 that constitute the gradient coil unit 152.

As described above, atomic nuclei aligned by an external magnetic field perform precession at a Larmor frequency, and a magnetization vector sum of multiple atomic nuclei may be designated by a single net magnetization M.

A Z-axis component of the net magnetization cannot be measured and only $M_{xy}$ is detectable. Thus, to acquire a magnetic resonance signal, excitation of atomic nuclei may be necessary to ensure that the net magnetization is present over an XY plane. For excitation of atomic nuclei, it may be necessary to apply an RF pulse tuned to a Larmor frequency to the static field.

The RF coil unit 153 includes a transmission coil to transmit an RF pulse and a reception coil to receive electromagnetic waves emitted from the excited atomic nuclei, i.e. a magnetic resonance signal.

The RF coil unit 153 is connected to the RF applicator 140, and the RF applicator 140 applies a drive signal to the RF coil unit 153 in response to a control signal transmitted from the pulse sequence controller 122 to enable transmission of the RF pulse.

The RF applicator 140 may include a modulator circuit to modulate an RF output signal into a pulse signal, and an RF power amplifier to amplify the pulse signal.

The RF coil unit 153 is also connected to the image processor 160. The image processor 160 includes a data collector 161 to receive data related to the magnetic resonance signal generated from the atomic nuclei, and a data processor 163 to form a magnetic resonance image by processing the received data.

The data collector 161 includes a preamplifier to amplify the magnetic resonance signal received by the reception coil of the RF coil unit 153, a phase detector to detect a phase upon receiving the magnetic resonance signal from the preamplifier, and an A/D converter to convert an analog signal acquired via the phase detection into a digital signal. The data collector 161 transmits the digitized magnetic resonance signal.

The image processor 160 further includes a data storage 162 to store a data space defined as a two-dimensional Fourier space. If all scanned data is completely stored in the data storage 162, the data processor 163 performs a two-dimensional inverse Fourier transform on the data within the two-dimensional Fourier space to reconstruct an image of the subject 200. The reconstructed image is displayed on the display unit 112.

A spin echo pulse sequence is mainly used to acquire a magnetic resonance signal from atomic nuclei. If the RF coil unit 153 sequentially applies a first RF pulse and a second RF pulse with an appropriate time interval Δt therebetween, the atomic nuclei show strong transverse magnetization after a time Δt has passed from application of the second RF pulse, which enables acquisition of a magnetic resonance signal. This is referred to as a spin echo pulse sequence, and the time taken after application of the first RF pulse and before generation of the magnetic resonance signal is referred to as a Time Echo (TE).

A flip angle of protons or atomic nuclei in the subject 200 may be represented as a 90° RF pulse, a 180° RF pulse, or the like based on the flip degree with respect to an axis where the protons or atomic nuclei are located before being flipped due to the application of such magnetic fields during MRI procedures described herein.

Figure 6:
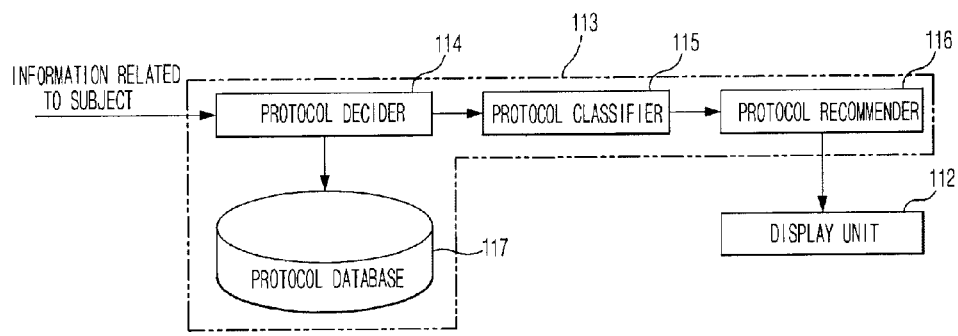
FIG. 6 is a block diagram illustrating a controller of the magnetic resonance imaging apparatus according to the exemplary embodiment of the present invention in more detail.

FIG. 6 is a block diagram illustrating the controller 113 of the magnetic resonance imaging apparatus 100 according to the exemplary embodiment of the present invention in more detail.

Information related to the subject 200 may be input via the operating console 111 of the workstation 110 by the operator, or may be automatically transmitted to the workstation 110 via a computer system of a facility using the MRI apparatus 100, such as a hospital's computer system. The controller 113 of the workstation 110 receives the transmitted information related to the subject 200.

Upon receiving the information related to the subject 200, a protocol decider 114 of the controller 113 analyzes the received information and determines appropriate protocols.

Information related to the subject 200, who may be a patient of a hospital, may include, for example, the sex, age, height, and weight of a patient, pregnancy status, disease history, and patient diagnosis information given by a medical team.

Although no medical record is present if a patient is a new patient who first visits a corresponding hospital, a previous medical record is present in the case of a second-visit patient, and therefore is transmitted, along with basic personal information of the patient, to the workstation 110.

Patient diagnosis information given by a medical team is information acquired as a medical team treats a patient, and may include, for example, a possible illness based on diagnosed results, diseased areas that are expected to cause diseases, and image capture protocols of the magnetic resonance imaging apparatus 100 for accurate confirmation of the diseases and the diseased areas.

Figure 7:
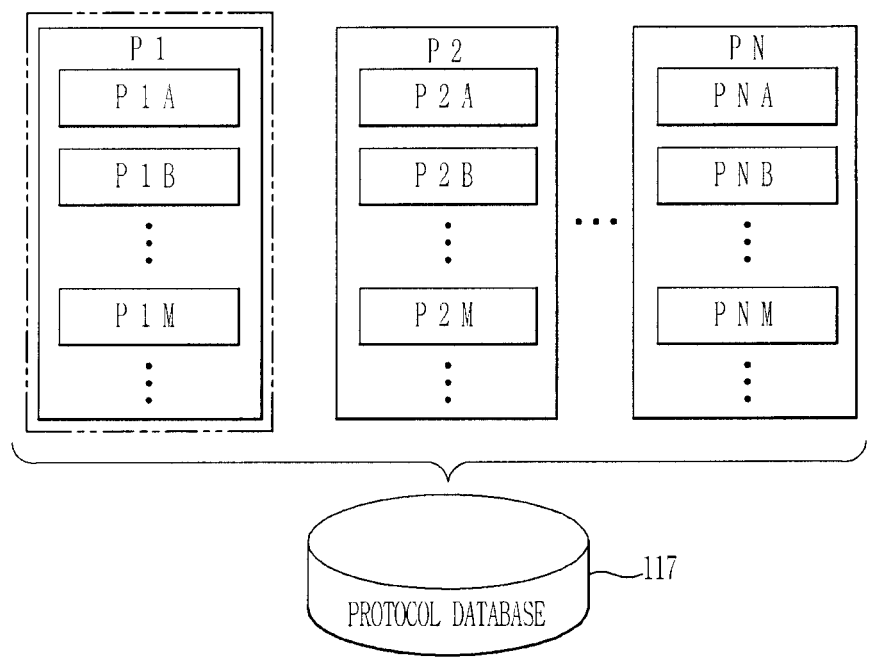
FIG. 7 is a view illustrating various kinds of protocols stored in a protocol database.

Protocols, which include a group of control signals representing pulse sequences, as shown in FIG. 5, are sent by the controller 113 to the pulse sequence controller 122, which in turn controls the applicators 130,140 to cause the coil units 151, 152, 153 to generate corresponding pulse sequences to generate the magnetic fields and waveforms as shown in FIG. 5. In the present invention, various protocols used for the magnetic resonance image capture of the subject 200 are preregistered in the magnetic resonance imaging apparatus 100 and are stored in a protocol database 117 and accessible by the protocol decider 114, the protocol classifier 115, and the protocol recommender 116. FIG. 7 illustrates various kinds of protocols stored in the protocol database 117. In FIG. 7, a total number of protocols N, in which N is a natural number of 1 or more, is stored in the protocol database 117.

For example, protocols to capture a magnetic resonance image of the same area are grouped and stored. That is, P1 may represent a group of protocols to capture an image of the liver, and P2 may represent a group of protocols to capture an image of the brain. Grouping and storing the protocols on a per image capture area basis is given by way of an illustrative example, and the protocols may be grouped and stored based on other criteria. Additional protocol groups, which may be labeled P3, P4, etc. may also be stored, and sub-groups of protocols within a main group may also be stored. For example, for group P1, sub-groups P1A, P1B, . . . P1M, in which M is a natural number of 1 or more, may be stored and arranged, with each sub-group representing a more specific group of protocols within the main group such as P1 for liver imaging protocols.

The protocol decider 114 receives and analyzes information related to the subject 200 to determine suitable protocols to capture an image of the subject 200 from among the protocols stored in the protocol database 117.

Figure 8:
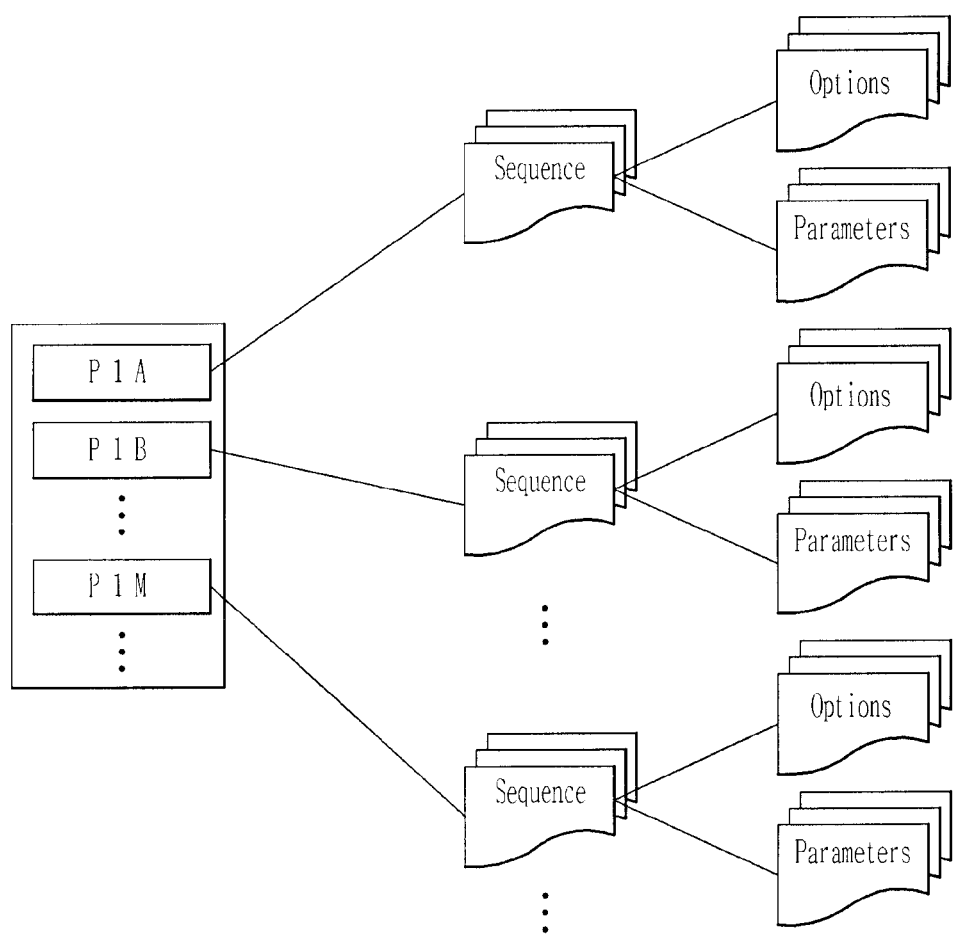
FIG. 8 is a view illustrating an organization of protocols.

FIG. 8 is a view illustrating an organization of protocols.

As described above, protocols may be understood as groups of sequences divided on a per image capture area basis for application to image the subject 200, and thus may be differently set according to different image capture areas of the subject 200. In addition, protocols to capture an image of the same area may be composed of different sequences, and may have different parameters or options.

In addition, protocols may be divided on a per image capture area basis with protocols to capture an image of the same area having different parameters or options even if such protocols are composed of the same sequence.

For example, a group of protocols to capture an image of the liver, designated by P1, may include various different protocols P1A, P1 B, . . . P1M as illustrated in FIG. 8, and the respective protocols may include multiple different sequences (e.g., Axial T2W FSE, Axial out of phase T1W FMPSPGR, and Axial in phase T1W FMPSPGR). Even in the case of the same sequence, the group of protocols may be changed based on options or parameters (e.g., TE, TR, ETL, Flip angle, voxel size, and scan time).

Although the magnetic resonance imaging apparatus 100 has been described as one example of a medical imaging apparatus, the technical ideas of the exemplary embodiments of the present invention are not limited to the magnetic resonance imaging apparatus 100, and may be applied to other medical imaging apparatuses, such as computed tomography apparatuses, X-ray image capture apparatuses, and the like. The above-described protocols are suited to characteristics of the magnetic resonance imaging apparatus 100, and it will be appreciated that image capture protocols of other medical imaging apparatuses may be set to suit the characteristics of the corresponding apparatus.

The protocol decider 114 in FIG. 6 determines an image capture area of the subject 200 based on patient diagnosis information given by a medical team, and selects protocols suitable for the determined image capture area from the protocol database 117. The protocol decider 114 may determine protocols more suitable for a patient based on personal information on the patient, such as the sex, age, height, and weight of the patient, pregnancy status, and diseases history.

For example, if an image capture area is determined to be the brain of the subject 200 based on diagnosis information given by a medical team, all protocols to capture an image of the brain are selected. Also, if an image capture area is determined to be the liver, all protocols to capture an image of the liver are selected. Among the selected protocols, protocols suitable for a patient based on personal information are determined as protocols to be recommended to the operator using the workstation 110.

Once the protocols have been determined, the protocols are classified based on various predefined criteria.

There are various criteria for classification of protocols. For example, the criteria for classification of protocols may include image capture time, resolution, image capture noise, power consumption, image quality, and the amount of data. It will be appreciated that the enumerated criteria are given by way of an illustrative example, and various other criteria may be possible.

A protocol classifier 115 serves to classify protocols based on various predefined criteria. For example, protocols may be classified from one having a short image capture time to one having a long image capture time, may be classified from one providing a general resolution image to one providing a high resolution image, may be classified from one generating small noise to one generating large noise during image capture, may be classified from one having low power consumption to one having high power consumption, may be classified from one providing only basic information to one including various analysis packages for implementation of high-grade analysis, and may be classified from one providing an image that occupies a small amount of data to one providing an image that occupies a large amount of data.

That is, if the operator selects a desired criterion, protocols classified based on the criterion may be recommended to the operator to allow the operator to select desired protocols from among the recommended protocols. The protocol classification criterion may be added and stored by the operator.

By predetermining and storing frequently used protocol classification criteria and classifying and providing protocols based on the criteria, it may be possible to assist the operator in more easily selecting protocols suitable for image capture of the subject 200.

Once the protocol classifier 115 has classified protocols based on various predefined criteria, a protocol recommender 116 automatically recommends the protocols to the operator by displaying the classified protocols via the display unit 112.

Figure 9:
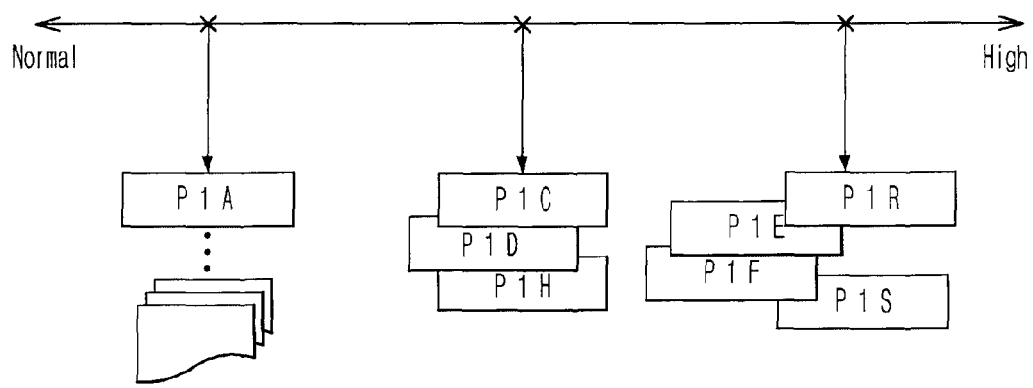
FIG. 9 is a view illustrating arrays of protocols classified on the basis of image quality.
Figure 10:
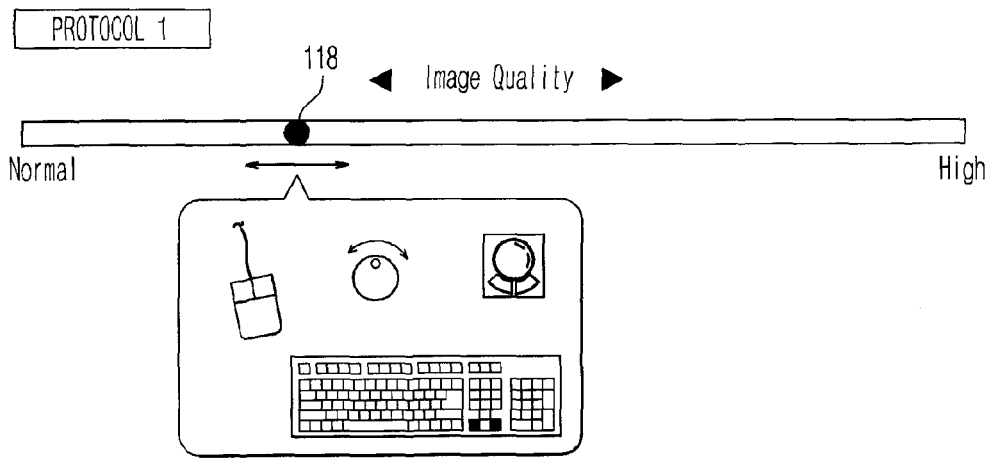
FIG. 10 is a view illustrating the protocols classified as illustrated in FIG. 9, which are displayed as a slide bar on a display unit.

FIG. 9 is a view illustrating arrays of protocols classified on the basis of image quality. FIG. 10 is a view illustrating the protocols classified as illustrated in FIG. 9 which are displayed as a slide bar on a screen of the display unit 112.

As illustrated in FIG. 9, if the operator selects image quality as a protocol recommendation criterion, the protocol recommender 116 sequentially aligns protocols from one providing a normal quality image, such as P1A, to one providing a high quality image, such as P1R and P1S, as well as P1E and P1F with slightly less image quality than P1R and P1S. Thus, alignment of protocols is carried out based on similarity of the protocols, using a predetermined similarity criterion, such as, in the present example, image quality, where image quality is measured by subjective or objective determiners, such as doctors evaluating MRI images, or a mathematical value determined by an image quality evaluating method known in the art. As illustrated in FIG. 9, only one protocol or a combination of multiple protocols may be recommended based on image quality.

The protocols aligned based on the predefined criterion, as illustrated in FIG. 9, may be displayed as a user interface on a screen in the form of a slide bar via the display unit 112 shown in FIG. 10.

If the operator moves an indicator 118 of the slide bar leftward or rightward via various input devices of the operating console, such as a mouse, a keyboard, a track ball, or a jog shuttle, as well as a touch screen using any type of touch screen known in the art, or icons such as the arrows shown in FIG. 10 and displayed on a graphic user interface (GUI) and/or on a touch screen, a protocol corresponding to the moved position is displayed on the display unit 112. This allows the operator to select a desired protocol from among the recommended protocols while directly confirming the displayed protocols.

Although FIG. 9 illustrates an array of protocols recommended by the protocol recommender 116, and selectable by the user interface in the form of the slide bar shown in FIG. 10, such access, display, and selection of protocols is given by way of an illustrative example and various other known shapes of user interfaces may be used to perform the same function.

Figure 11:
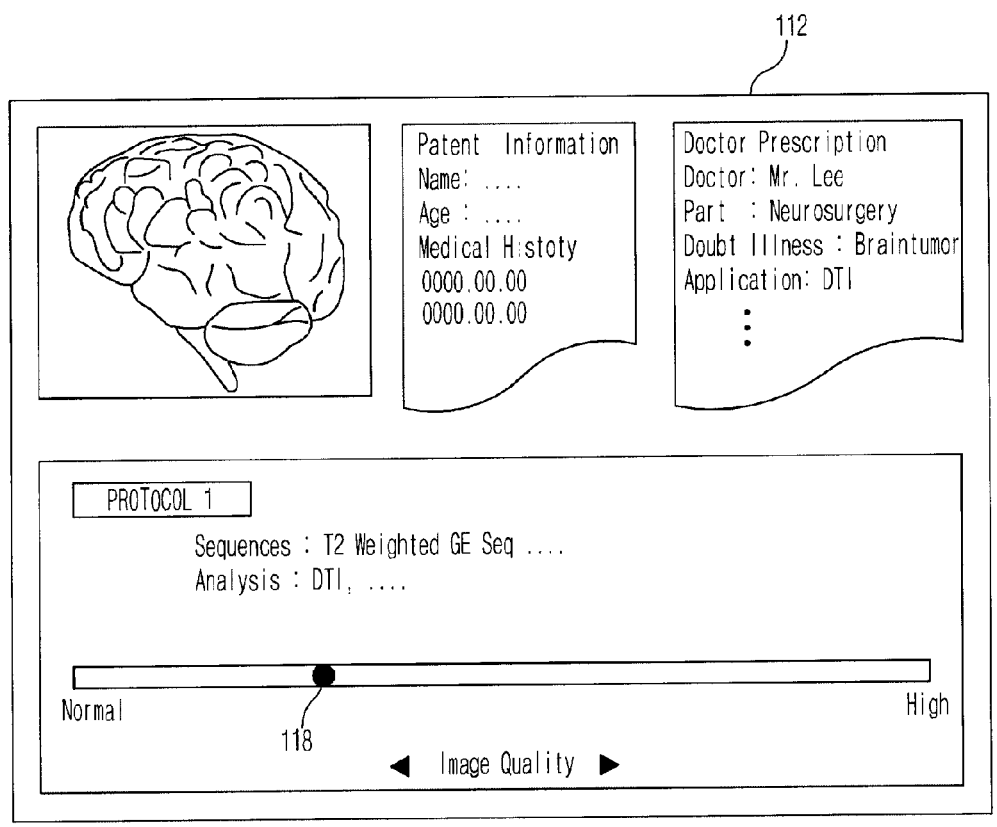
FIG. 11 is a view illustrating an exemplary embodiment of a protocol recommendation interface displayed on the display unit.

FIG. 11 is a view illustrating an exemplary embodiment of a protocol recommendation interface displayed on the screen of the display unit 112.

A representative image of an image capture area, information on a patient, diagnosis information given by a medical team, recommended protocols and the like may be displayed respectively in divided regions of the interface.

As described above, protocols aligned based on a predefined criterion are displayed via the user interface in FIG. 11 in the form of the slide bar with the indicator 118. If the operator moves the indicator 118 of the slide bar leftward or rightward via various input devices described herein, the protocol corresponding to the moved position is displayed as constituent sequences of the protocol and analysis tool illustrated in FIG. 11.

Although FIG. 11 illustrates image quality as a protocol classification criterion, this protocol classification criterion is given by way of an illustrative example, and if another classification criterion is selected, protocols classified to suit the criterion are displayed. When it is desired to select another classification criterion, the operator may click arrows at opposite sides of a currently displayed classification criterion to change to another classification criterion.

Figure 12:
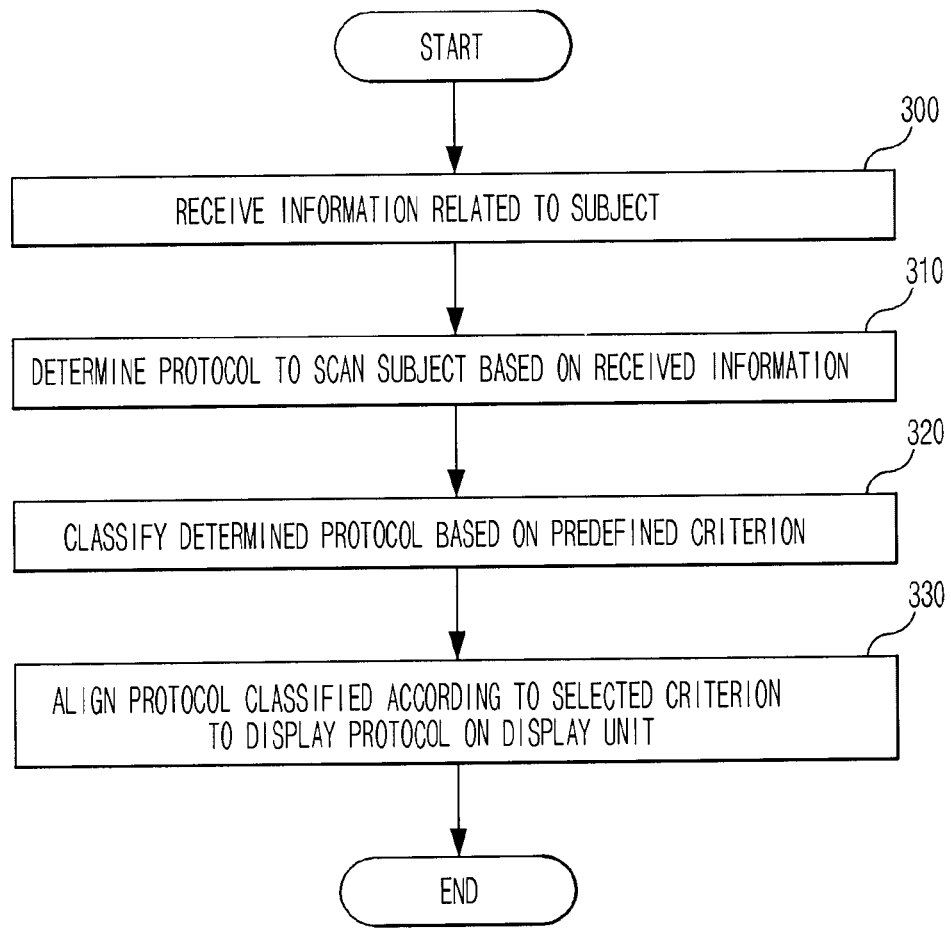
FIG. 12 is a flowchart illustrating a control method of the magnetic resonance imaging apparatus according to the exemplary embodiment of the present invention.

FIG. 12 is a flowchart illustrating a control method of the magnetic resonance imaging apparatus 100 according to the exemplary embodiment of the present invention.

Referring to FIG. 12 in conjunction with FIGS. 1-11 and the description thereof, the controller 113 of the workstation 110 receives information related to the subject 200 in step 300.

If information related to the subject is received in step 300, the controller 113 analyzes the received information and determines protocols suitable for the analyzed information in step 310.

Once the protocols have been determined in step 310, the protocols are classified based on various predefined criteria by the controller 113 in step 320.

Once the protocol classifier has classified protocols based on various predefined criteria in step 320, the controller 113 automatically recommends the protocols to the operator by aligning the protocols classified according to the selected criterion for displaying the classified protocols via the display unit 112 in step 330, and the method then ends.

Although the magnetic resonance imaging apparatus has been described as one example of a medical imaging apparatus, the technical ideas of the exemplary embodiments of the present invention are not limited to the magnetic resonance imaging apparatus and may be applied to various other medical imaging apparatuses, such as computed tomography apparatuses, X-ray image capture apparatuses, and the like.

As is apparent from the above description, according to an aspect of the present invention, protocols suited to a subject 200 or patient, based on information on the patient and an instruction of a medical team, are automatically recommended, which may reduce a time required for selection of protocols.

Further, as a result of recommending various protocols classified based on a predefined criterion, it may be possible to more accurately select protocols suitable for diagnosis.

The above-described apparatus and methods according to the present invention can be implemented in hardware or firmware, or as software or computer code, or combinations thereof. In addition, the software or computer code can also be stored in a non-transitory recording medium such as a CD ROM, a RAM, a ROM whether erasable or rewritable or not, a floppy disk, CDs, DVDs, memory chips, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software, computer code, software modules, software objects, instructions, applications, applets, apps, etc. that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include volatile and/or non-volatile storage and memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, the program may be electronically transferred through any medium such as communication signals transmitted by wire/wireless connections, and their equivalents. The programs and computer readable recording medium can also be distributed in network-coupled computer systems so that the computer readable code is stored and executed in a distributed fashion.

Although the embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A medical imaging apparatus comprising:
    a workstation for receiving information related to a subject, the workstation including:

an operating console that receives a selection of a subject criterion;
a controller which receives and analyzes the received subject criterion and determines a plurality of protocols to scan the subject, classifies the plurality of determined protocols based on a plurality of predefined classification criteria into a plurality of selectable groups or sub-groups of protocols, and sequentially aligns for display and recommends the classified plurality of determined protocols grouped according to a selected classification criterion for the subject,
wherein the controller sequentially aligns for display the selectable groups or sub-groups of determined protocols based on a similarity between the plurality of determined protocols using a predetermined similarity criterion comprising at least one of an image quality as measured by subjective or objective determiners, or a mathematical value determined by an image quality evaluating method; and
a display unit which displays an array of the selectable groups or sub-groups of the sequentially aligned and classified plurality of determined protocols recommended by the controller,
wherein in response to movement of an indicator to a position on a screen of the display unit, a particular protocol corresponding to a moved position of the indicator is displayed as constituent sequences of the particular protocol to provide an analysis tool of the protocol,
wherein the operating console receives a selection of one of a selected group or a sub-group of the displayed selectable groups or sub-groups of protocols recommended by the controller; and
a medical image generating apparatus which uses the selected group or sub-group of protocols for generating and outputting an image of a portion of the subject,
wherein the plurality of predefined classification criteria to classify the plurality of protocols include image capture time, resolution, image capture noise, power consumption, image quality, and an amount of data.

2. The apparatus according to claim 1, wherein the controller receives and analyzes the information related to the subject to determine information required to scan the subject, and determines the plurality of determined protocols to scan the subject based on the determined information.

3. The apparatus according to claim 2, wherein the information related to the subject includes a sex, age, and medical record of the subject, and includes subject diagnosis information given by a medical team.

4. The apparatus according to claim 3, wherein the diagnosis information includes information on diseased areas, a possible illness, and a plurality of selected protocols selected by a medical team.

5. The apparatus according to claim 1, wherein the display unit displays an image related to an image capture area of the subject, information related to the subject, diagnosis information given by a medical team, and the array of the selectable groups of the plurality of determined protocols recommended by the controller.

6. The apparatus according to claim 1, wherein the display unit displays a user interface to allow a selection of a group or subgroup of a desired protocol from among the array of the selectable groups of determined protocols.

7. A control method of a medical imaging apparatus, the control method comprising:

receiving at a workstation information related to a subject;
receiving at a physical operating console of the workstation, an input selection of a subject criterion of the medical imaging apparatus;
receiving and analyzing by a physical controller of the workstation the received subject criterion and determining a plurality of protocols to scan the subject using the received information;
classifying by the physical controller, the plurality of determined protocols based on a plurality of predefined classification criteria into a plurality of selectable groups or sub-groups of protocols;
sequentially aligning for display the selectable groups or sub-groups of determined protocols based on a similarity between the plurality of determined protocols using a predetermined similarity criterion comprising at least one of an image quality as measured by subjective or objective determiners, or a mathematical value determined by an image quality evaluating method and recommending the sequentially aligned and classified plurality of determined protocols grouped according to the predefined classification criteria for the selected subject;
displaying an array of the selectable groups or sub-groups of the sequentially aligned and classified plurality of determined protocols on a physical display unit of the work station;
receiving, at the operating console, a selection of one of a selected group or a sub-group of the displayed selectable groups or sub-groups recommended by the physical controller
wherein in response to movement of an indicator to a position on a screen of the display unit, displaying a particular protocol corresponding to a moved position of the indicator as constituent sequences of the particular protocol to provide an analysis tool of the protocol; and
generating and outputting an image of a portion of the subject using a physical image generating apparatus which uses the selected group or sub-group of sequentially aligned and recommended classified plurality of determined protocols, wherein the classification criteria of the plurality of protocols include image capture time, resolution, image capture noise, power consumption, image quality, and the amount of data.

8. The control method according to claim 7, wherein determining the plurality of protocols to scan the subject includes:
receiving and analyzing the information related to the subject to determine information required to scan the subject; and
determining the plurality of protocols to scan the subject based on the determined information.

9. The control method according to claim 8, wherein the information related to the subject includes a sex, age, and medical record of the subject, and includes subject diagnosis information given by a medical team.

10. The control method according to claim 9, wherein the diagnosis information includes information on diseased areas, a possible illness, and a plurality of selected protocols selected by a medical team.

11. The control method according to claim 7, further comprising displaying an array of the recommended plurality of determined protocols, an image related to an image capture area of the subject, information related to the subject, and diagnosis information given by a medical team on a display unit.

12. The control method according to claim 11, wherein displaying the array of the selectable groups or sub-groups of determined protocols on the display unit includes displaying, on the display unit, the plurality of determined protocols sequentially aligned and recommended via a user interface to allow selection of a desired protocol from among the array of the selectable groups or sub-groups of determined protocols recommended by the physical controller.

* * * * *